(12) United States Patent
Deboeuf et al.

(10) Patent No.: US 10,449,007 B2
(45) Date of Patent: Oct. 22, 2019

(54) ROBOTIC SYSTEM FOR ARTERIOGRAPHY, ROBOT AND ROTARY DRIVE PART FOR SUCH A ROBOTIC SYSTEM

(71) Applicant: ROBOCATH, Rouen (FR)

(72) Inventors: Sébastien Deboeuf, Sotteville-les-Rouen (FR); Jacques Marignier, Le Mesnil Esnard (FR); Julien Maurel, Bonsecours (FR); Bruno Fournier, Saint Ouen (FR); Philippe Bencteux, Saint Martin du Vivier (FR)

(73) Assignee: ROBOCATH, Rouen (FR)

(*) Notice: Subject to any disclaimer, the term of this patent is extended or adjusted under 35 U.S.C. 154(b) by 263 days.

(21) Appl. No.: 15/322,414

(22) PCT Filed: Jun. 26, 2015

(86) PCT No.: PCT/FR2015/051743
§ 371 (c)(1),
(2) Date: Dec. 27, 2016

(87) PCT Pub. No.: WO2015/197996
PCT Pub. Date: Dec. 30, 2015

(65) Prior Publication Data
US 2017/0156802 A1 Jun. 8, 2017

(51) Int. Cl.
*A61B 34/30* (2016.01)
*A61B 6/00* (2006.01)
(Continued)

(52) U.S. Cl.
CPC .............. *A61B 34/30* (2016.02); *A61B 6/481* (2013.01); *A61B 6/504* (2013.01); *A61M 5/007* (2013.01);
(Continued)

(58) Field of Classification Search
USPC ......... 604/523, 508, 95.01, 96.01, 264, 349, 604/164.13, 95.03, 171; 600/433, 434,
(Continued)

(56) References Cited

U.S. PATENT DOCUMENTS 7,887,549 B2 * 2/2011 Wenderow ......... A61M 25/0113
600/585
9,192,745 B2 * 11/2015 Bencteux ........... A61M 25/0113
(Continued)

FOREIGN PATENT DOCUMENTS

EP 1792638 A2 6/2007
EP 2567670 A1 3/2013
(Continued)

OTHER PUBLICATIONS

French Search Report Application No. FR 14 56042 dated Feb. 25, 2015.
(Continued)

*Primary Examiner* — Jorge L Carrasquillo
(74) *Attorney, Agent, or Firm* — Miller, Matthias & Hull LLP (57) ABSTRACT

The robot for arteriography comprises a fixed base and a movable receptacle. The receptacle comprises a recipient receiving an elongate flexible member. A drive system drives the receptacle relative to the base. The receptacle comprises a drive module rigidly connected to the elongate flexible member in translation in operational configuration of the robot. The drive module is actuated in order to generate a rotational movement of the elongate flexible member.

27 Claims, 4 Drawing Sheets

(51) Int. Cl.
   *A61M 5/00*    (2006.01)
   *A61M 25/01*   (2006.01)
   *A61M 25/09*   (2006.01)
   *A61B 17/00*       (2006.01)

(52) U.S. Cl.
   CPC ..... *A61M 25/0113* (2013.01); *A61M 25/0116* (2013.01); *A61M 25/09041* (2013.01); *A61B 2017/0023* (2013.01); *A61B 2034/301* (2016.02)

(58) Field of Classification Search
   USPC .............................. 600/435, 466, 585, 139
   See application file for complete search history.

(56) References Cited

U.S. PATENT DOCUMENTS

| | | | | |
|---|---|---|---|---|
| 2003/0176770 | A1* | 9/2003 | Merril | A61B 34/70 |
| | | | | 600/118 |
| 2007/0123070 | A1 | 5/2007 | Bencteux | |
| 2011/0130718 | A1* | 6/2011 | Kidd | A61M 25/0105 |
| | | | | 604/95.01 |
| 2011/0166513 | A1* | 7/2011 | Cohen | A61M 25/0105 |
| | | | | 604/95.01 |
| 2013/0172713 | A1 | 7/2013 | Kirschenman | |
| 2013/0172738 | A1 | 7/2013 | Robocath | |
| 2014/0066900 | A1* | 3/2014 | Blacker | A61M 25/0147 |
| | | | | 604/510 |
| 2014/0220683 | A1 | 8/2014 | Hemarina | |
| 2015/0327938 | A1 | 11/2015 | Robocath | |
| 2016/0008076 | A1 | 1/2016 | Robocath | |
| 2016/0008077 | A1 | 1/2016 | Robocath | |
| 2016/0008574 | A1 | 1/2016 | Bencteux et al. | |

FOREIGN PATENT DOCUMENTS

| | | |
|---|---|---|
| FR | 2979352 A1 | 3/2013 |
| WO | 2005117596 A2 | 12/2005 |
| WO | 2009137410 A1 | 11/2009 |
| WO | 2014096731 A1 | 6/2014 |

OTHER PUBLICATIONS

International Search Report Application No. PCT/FR2015/051743 reported on Oct. 26, 2010.

* cited by examiner

ROBOTIC SYSTEM FOR ARTERIOGRAPHY, ROBOT AND ROTARY DRIVE PART FOR SUCH A ROBOTIC SYSTEM

CROSS-REFERENCE TO RELATED APPLICATION

This Application is a 35 USC § 371 US National Stage filing of International Application No. PCT/FR2015/051743 filed on Jun. 26, 2015, and claims priority under the Paris Convention to French Patent Application No. 14 56042 filed on Jun. 27, 2014.

FIELD OF THE DISCLOSURE

This invention relates to robotic systems for arteriography, to robots and to the rotation drive parts for such robotic systems.

BACKGROUND OF THE DISCLOSURE

Such robots drive elongate flexible medical members. A typical example of an elongate flexible medical member is for example a catheter. Such a catheter has to be introduced into an anatomical duct of a patient, and therefore must be relatively flexible. The end of the catheter must also reach an internal organ of the patient, the catheter must therefore be relatively elongate. Other examples of elongate flexible medical members are for example a guide, which is of lesser diameter, and generally arranged inside the catheter, at least inside the body of the patient, and whereon the latter slides, or an interventional catheter, also arranged inside the catheter, and of which the end provides a certain medical function such as a medical tool (clip, balloon, etc.).

The insertion of such catheters is generally monitored with X-rays. This results in a certain irradiation of the doctor practicing such insertions repeatedly.

Efforts have been made to robotise this insertion. EP 1 792 638 describes an example of such efforts. As such, the manipulation of the catheter is provided by the robot, which is remotely controlled by the doctor, still under X-ray guidance, but in a non-radiated room.

EP 1 792 368 describes a system wherein a dedicated drive module manages both the translation and the rotation of the guide. Another dedicated drive module manages both the translation and the rotation of the catheter. WO 2014/096,731 and EP 2 567 670 present improvements of this architecture.

Although the robot shown hereinabove provides entire satisfaction, it is still sought to simplify the design. Indeed, it is sought to limit as much as possible the mechanisms that come into play in the robotisation, mainly for reasons of safety for the patient (minimisation of the risk of a breakdown).

In another sector of activity, so called electrophysiology catheters are implemented. US 2011/130,718 and US 2013/172,713 are two examples of such realisations. These electrophysiology catheters are complex systems that require remote actuation (operation of a tool at the end of the electrophysiology catheter or bending of the head of the electrophysiology catheter). This results in that the control mechanism is very complex, in that it has to manage the displacement of the electrophysiology catheter, as well as its actuation independently of its position. As such, the issues to be resolved are different.

SUMMARY OF THE DISCLOSURE

This invention has in particular for purpose to simplify the design of a robotic catheterisation system that manages the displacement of the catheter.

To this effect, according to the invention, a robotic catheterisation system is provided comprising an elongate flexible member to be introduced inside the patient and a catheterisation robot, The elongate flexible member comprising a flexible tube and being connected to a rotation drive part, the rotation drive part comprising a gear connected to the flexible tube, having a hole and a first rotation drive surface, and a hollow connector connected to the drive part, downstream of the latter, and allowing for the passage of a guide through the connector and to the hole of the gear, with the catheterisation robot comprising:
a fixed base,
a receptacle mounted movable relative to the fixed base according to at least one degree of freedom,
the receptacle being suited to receive said elongate flexible member to be introduced inside a patient,
a drive system suitable for driving the receptacle relative to the base along the degree of freedom,
the receptacle further comprising a drive module, the drive module having a longitudinal axis for the passage of the elongate flexible member, the drive module being connected to the elongate flexible member in translation along the longitudinal axis of passage in the operating configuration of the robot, the drive module comprising a rotation drive member comprising a pinion directly or indirectly motorised, and comprising a second rotation drive surface, the pinion meshing with the gear of the rotation drive part connected to the elongate flexible member, with the drive module being actuatable in order to generate a rotational movement of the elongate flexible member about the longitudinal axis of passage, the first and second rotation drive surfaces cooperating in order to transmit a rotation command from the rotation drive member in a rotational movement of the elongate flexible member about the longitudinal axis of passage.

Thanks to these arrangements, a robotic system is provided which, while still allowing the same functions as the known system, comprises fewer mechanisms.

An advantage of this embodiment is to allow for easier decontamination of the robot.

In preferred embodiments of the invention, recourse may possibly be had furthermore to one and/or to the other of the following arrangements:

said rotation drive part comprises a first axial retention portion, and wherein the drive module comprises a second axial retention portion, with the first and second axial retention portions cooperating in order to axially retain the elongate flexible member relative to the drive module along the longitudinal axis of passage;

the first axial retention portion of the rotation drive part comprises a first front abutment directed towards the front and a first rear abutment directed towards the rear, the second axial retention portion of the drive module comprises a second front abutment, directed towards the rear, and a second rear abutment directed towards the front, the first and second front abutments cooperate in order to prevent a displacement towards the front of the elongate flexible member relative to the drive module, the first and second rear abutments cooperate in order to prevent a displacement towards the rear of the elongate flexible member relative to the drive module;

the drive part is carried out as a consumable part that can be assembled/disassembled from the drive module;

the flexible tube is hollow;

the drive part comprises an upstream mechanical assembly for assembly to the elongate flexible medical member, a gear, a ring, a downstream mechanical assembly for assembly to a guide introducing connector, and the upstream mechanical assembly, the gear, the ring or the downstream mechanical assembly, or a component comprised of at least two of these elements is carried out as or is part of a consumable item that can be assembled/disassembled from the drive module;

the drive module comprises a body and a cover removably mounted relative to the body, with the cover able to have alternatively, relative to the body, an assembled configuration wherein the drive module is connected to the elongate flexible member in translation according to the longitudinal axis of passage, and an open configuration wherein the elongate flexible member can be assembled to the or disassembled from the drive module;

the base defines a channel comprising a guide wall of the elongate flexible member, with the guide wall cooperating with the elongate flexible member in order to guide a movement of translation of the elongate flexible member relative to the base during the movement of the receptacle relative to the base along the degree of freedom;

the receptacle comprises a recipient suited for receiving said elongate flexible member, with the drive module being fixed to the recipient;

the elongate flexible member is a first elongate flexible member, the drive module is a first drive module, the robotic system further comprising a second elongate flexible member to be introduced inside the patient, with the receptacle being suited to receive said second elongate flexible member to be introduced inside a patient, the receptacle further comprising a second drive module, the second drive module being actuatable in order to generate two separate movements of translation and of rotation of the second elongate flexible member relative to the second recipient;

the first elongate flexible member comprises an access opening through which the second elongate flexible member extends;

the receptacle comprises a recipient, the second drive module is fixed to the recipient, and the second drive module can be actuated in order to generate the movements of the second elongate flexible member relative to the recipient;

the drive module is carried out as or is a part of a consumable item that can be assembled/disassembled from the recipient.

According to another aspect, the invention relates to a catheterisation robot comprising the characteristics of the catheterisation robot such as defined hereinabove.

According to another aspect, the invention relates to a part for driving in rotation comprising:

a fastening portion suited for fastening the rotation drive part to a flexible tube of an upstream hollow elongate flexible medical member, a gear rigidly connected to the fastening portion, having a central hole intended to be in communication with the hollow inside of the flexible tube, and a first rotation drive surface, a fastening portion suited to fasten the rotation drive part to a downstream hollow connector, and allowing for the passage of a guide wire through the connector and to the hole of the gear.

In preferred embodiments of the invention, recourse may possibly further be had to one and/or the other of the following arrangements:

the gear has an axis, the rotation drive part further comprising a continuous closed cylindrical ring comprising a central hole in communication with the hole of the gear, and suited for guiding the rotation drive part around said axis;

the ring is downstream of the gear;

the ring is upstream of the portion for fastening;

the ring comprises an outer peripheral surface cylindrical in guiding revolution;

the ring comprises a front abutment surface directed towards the front of the ring and a rear abutment surface, directed towards the rear of the ring;

the fastening portion is suited for fastening the rotation drive part to the connector by allowing for the rotation of the drive part relative to the connector about a longitudinal axis, while still maintaining the seal for the purposes of fluidic communication;

the fastening portions are complementary with one another.

According to another aspect, the invention relates to a system comprising such a rotation drive part and a connector rigidly connected to the rotation drive part, allowing for the passage of a guide wire through the connector and to the hole of the gear, the connector comprising a fastening portion suited to cooperate with the fastening portion of the rotation drive part in order to fasten the rotation drive part to the connector.

In preferred embodiments of the invention, recourse may eventually further be had to one and/or the other of the following arrangements:

the connector comprises a bypass inlet making it possible to place the inside of the hollow elongate flexible medical member in fluidic communication with an external circuit for the injection of contrast fluid inside the flexible tube;

this system, or a system comprising such a rotation drive part further comprises a hollow elongate flexible medical member provided with a flexible tube and with a fastening portion, suitable for cooperating with the fastening portion of the rotation drive part in order to fasten the rotation drive part to the flexible tube.

BRIEF DESCRIPTION OF THE DRAWINGS

Other characteristics and advantages of the invention shall appear during the following description of one of its embodiments, provided as a non-limiting example, with regards to the attached drawings.

In the drawings.

DETAILED DESCRIPTION OF THE DISCLOSURE

In the various figures, the same references designate identical or similar elements.

Figure 1:
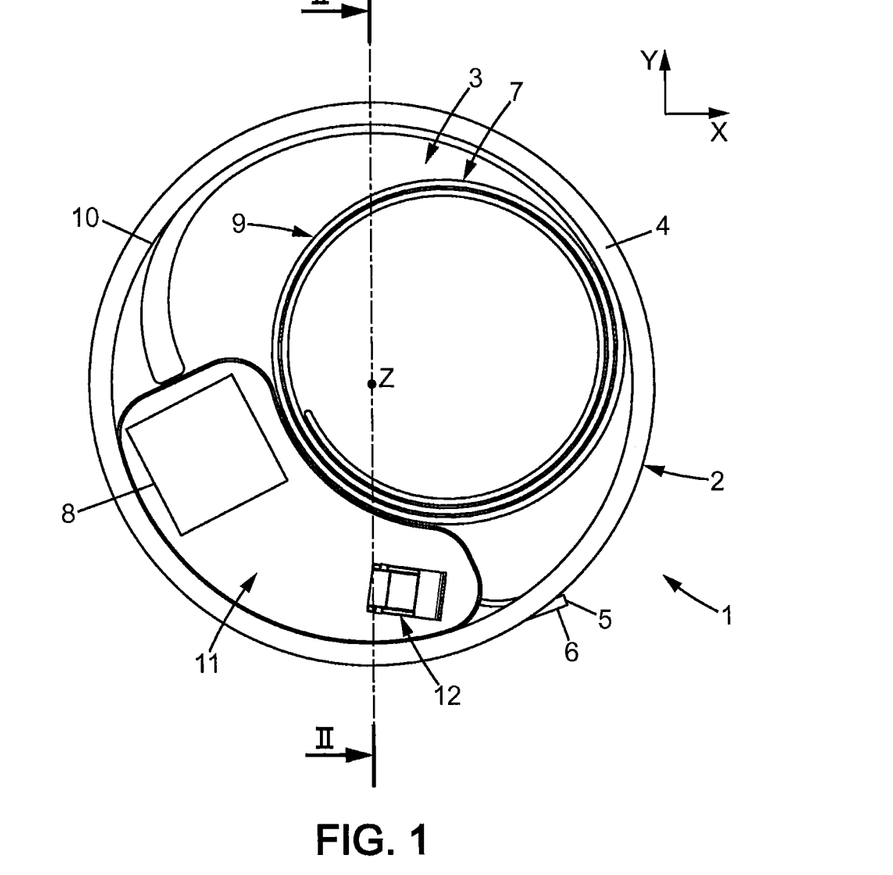
FIG. 1 is a partial diagrammatical top view of a robot for arteriography.

FIG. 1 diagrammatically shows a catheterisation robot 1 that can be used for an arteriography. The robot 1 comprises a fixed base 2 and a receptacle 3 movable relative to the base. The base 2 is referred to as fixed in order to serve as a reference to the movement of the receptacle, which moves relative to the base. However, it cannot be excluded that the base 2 itself can be displaced in certain conditions. In this example, the base 2 is fixed relative to the patient in the process of medical intervention (arteriography). In this case, the fixed base 2 comprises an outer peripheral crown 4 centred on an axis Z, for example vertical. The receptacle 3 is movable in rotation relative to the base 2 around the axis Z. The base 2 comprises an outlet port 5 of which the position is fixed relative to the patient in the process of intervention. The port 5 is for example provided with a channel 6 which protrudes radially outwards from the crown 4.

The receptacle 3 is suited to contain an elongate flexible medical member. By elongate flexible medical member, reference is made for to a catheter, which comprises a hollow tube intended to be introduced into a channel (in particular an artery) of a patient. Another example of elongate flexible medical member is an interventional catheter that adds to a conventional catheter a medicalised function, such as an inflatable balloon, a cutting tool, etc. Another example of elongate flexible medical member is for example a guide wire, or guide, in the form of a wire with a diameter less than that of the catheter, solid, and around which the catheter is intended to be displaced coaxially inside the body of the patient.

In order to contain such an elongate flexible medical member, the receptacle 3 will for example by carried out sterile and can contain a conservation liquid such as physiological fluid wherein the elongate flexible medical member will bathe. For example a guiding channel in the receptacle 3 is provided.

More precisely, the example shown provides that the receptacle 3 is suited to contain both two elongate flexible medical members intended to be coaxial inside the body of the patient. In order to set the ideas, the radially interior elongate flexible medical member shall be called the "guide" and the radially exterior elongate flexible medical member the "catheter", even if other configurations are possible.

The receptacle 3 therefore comprises a first channel 7 opening onto a first drive module 8. The first channel 7 can comprise a rear portion 9 and a front portion 10 in continuity with the rear portion, and opening onto the first drive module 8. The rear portion 9 extends for example in the shape of a spiral comprising one or several turns. Alternatively, shapes other than a channel can be provided, if suitable. As it stems from the description hereinabove, the implementation of a recipient as comprising a receptacle is only one embodiment. Alternatively, the receptacle 3 receives the elongate flexible medical member in any suitable way.

The first drive module 8 is of any suitable shape. This can be for example a drive module such as described in application EP 1 792 638 referenced hereinabove. The description of the drive module in this document in integrated by reference into this application. Such a drive module is able to alternatively generate:

A translation of the guide according to a longitudinal axis,
A rotation of the guide around its longitudinal axis, Of course, the longitudinal axis in question is the one of the guides on the drive module 8, but such movements generated on the drive module 8 cause equivalent movements of the end of the guide inside the patient.

The receptacle 3 also comprises a recipient 11 for the catheter. The receptacle 3 comprises a second drive module 12 suitable for driving the catheter in rotation around its longitudinal axis.

In the example shown, the recipient 11 comprises a first inlet channel 13 that extends from the second drive module 12 towards a peripheral channel 14. The recipient 11 also comprises the peripheral channel 14. The peripheral channel 14 can extend over practically all of the periphery of the receptacle 3.

Figure 2:
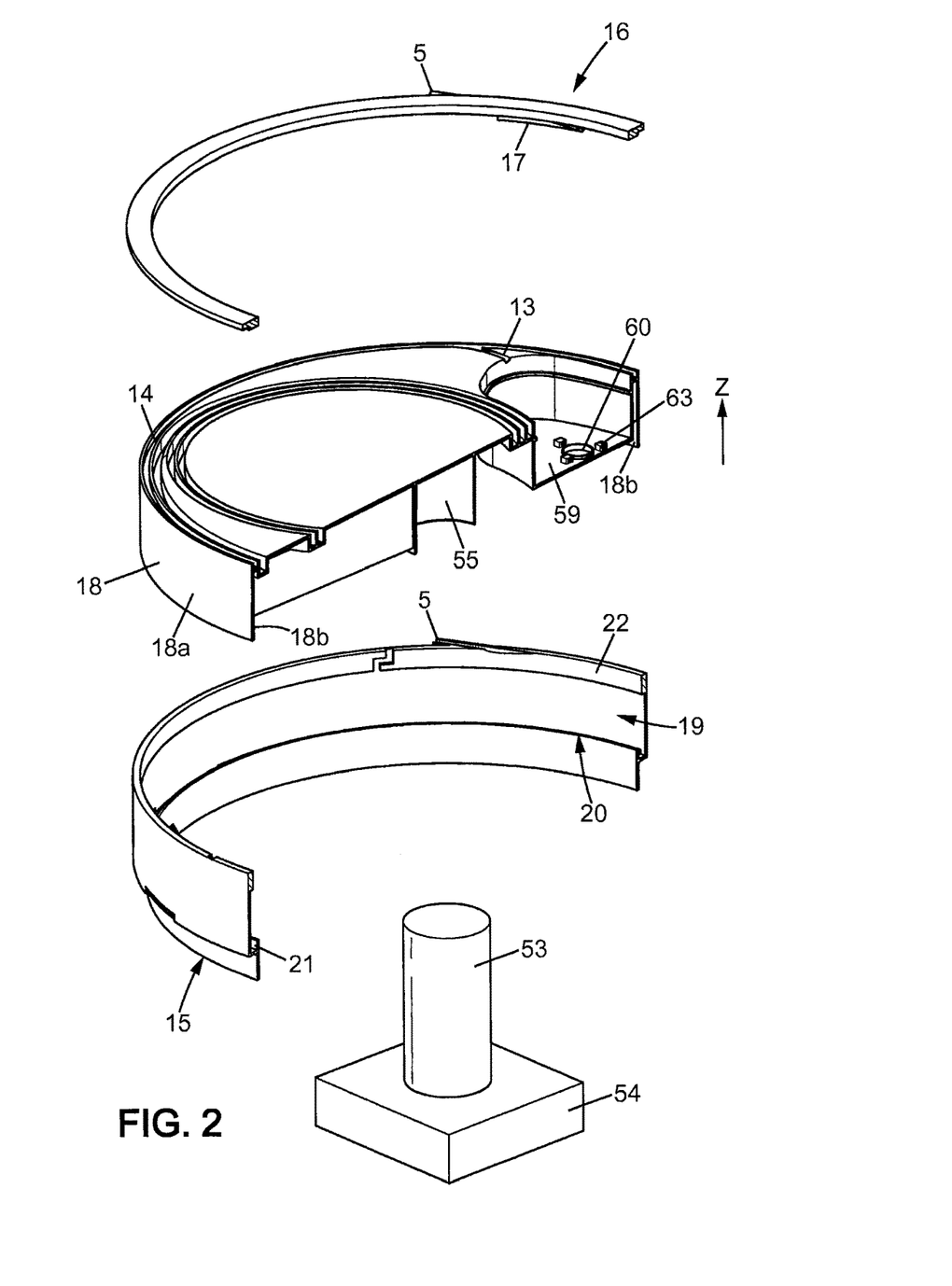
FIG. 2 is a cross-section view according to the line II-II in FIG. 1, in perspective, exploded, of the robot of FIG. 1.

As can be seen in FIG. 2, the base 2 comprises a base 15 and a cover 16 integral with one another. The cover 16 extends above the peripheral channel 14. A deflector 17 is rigidly connected to the base 2. In the assembled configuration of the robot, the deflector 17 extends in the peripheral channel 14. The deflector 17 is for example protruding downwards from the lower face of the cover 16. The deflector comprises a guiding surface suited for guiding the catheter outside of the peripheral channel 14 in the direction of the port 5. As such, the base 2 comprises a through-opening extending from the deflector 17 to the port 5. The through-opening in question, forming a channel 6, can be formed partially in the base 15 and partially in the cover 16.

In the configuration shown, which corresponds to the configuration at the beginning of the intervention, the deflector 17 is located, in the peripheral channel 14, adjacent to the inlet channel 13.

The base 2 and the receptacle 3 also cooperate for the guiding in rotation of the base 2 and of the receptacle 3. For example, the receptacle 3 comprises an outer peripheral wall 18 comprising an outer peripheral surface 18a cylindrical of revolution and an inner peripheral surface 18b cylindrical of revolution. The base 2 forms a guiding groove 19 comprising an inner peripheral wall 20 of which a first guiding surface 21 is radially turned outwards, and of which a second guiding surface 22 is turned radially inwards by being radially offset outwards relative to the first guiding surface 21 by at least the thickness of the outer peripheral wall 18. The outer peripheral wall 18 is consequently guided in rotation around the axis Z relative to the base 2:

By cooperation of the first guiding surface 21 with the inner peripheral surface 18b, and
By cooperation of the second guiding surface 22 with the outer peripheral surface 18a.

These two cooperations can in addition be offset from one another according to the axis Z.

The peripheral wall 18 is in addition supported in a sliding manner in the bottom of the groove 19.

Alternatively, the base 2 and the receptacle 3 cooperate for the guiding of the base 2 and of the receptacle 3 according to any suitable degree of freedom.

The driving, for example in relative rotation, of the receptacle 3 and of the base 2 can be motorised. For example, a drive system is provided comprising a shaft 53 of axis Z rigidly connected to the receptacle 3, and driven in rotation by a motor 54 rigidly connected to the base. The shaft 53 is for example force-fitted into a lower sleeve 55 of the receptacle 3.

Figure 3:
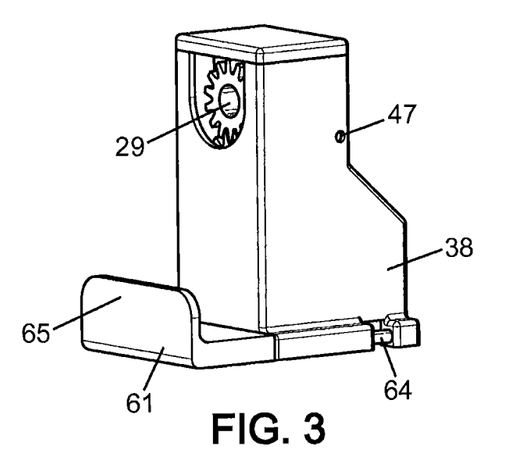
FIG. 3 is a perspective view of a drive module for the robot of FIGS. 1 and 2.
Figure 4:
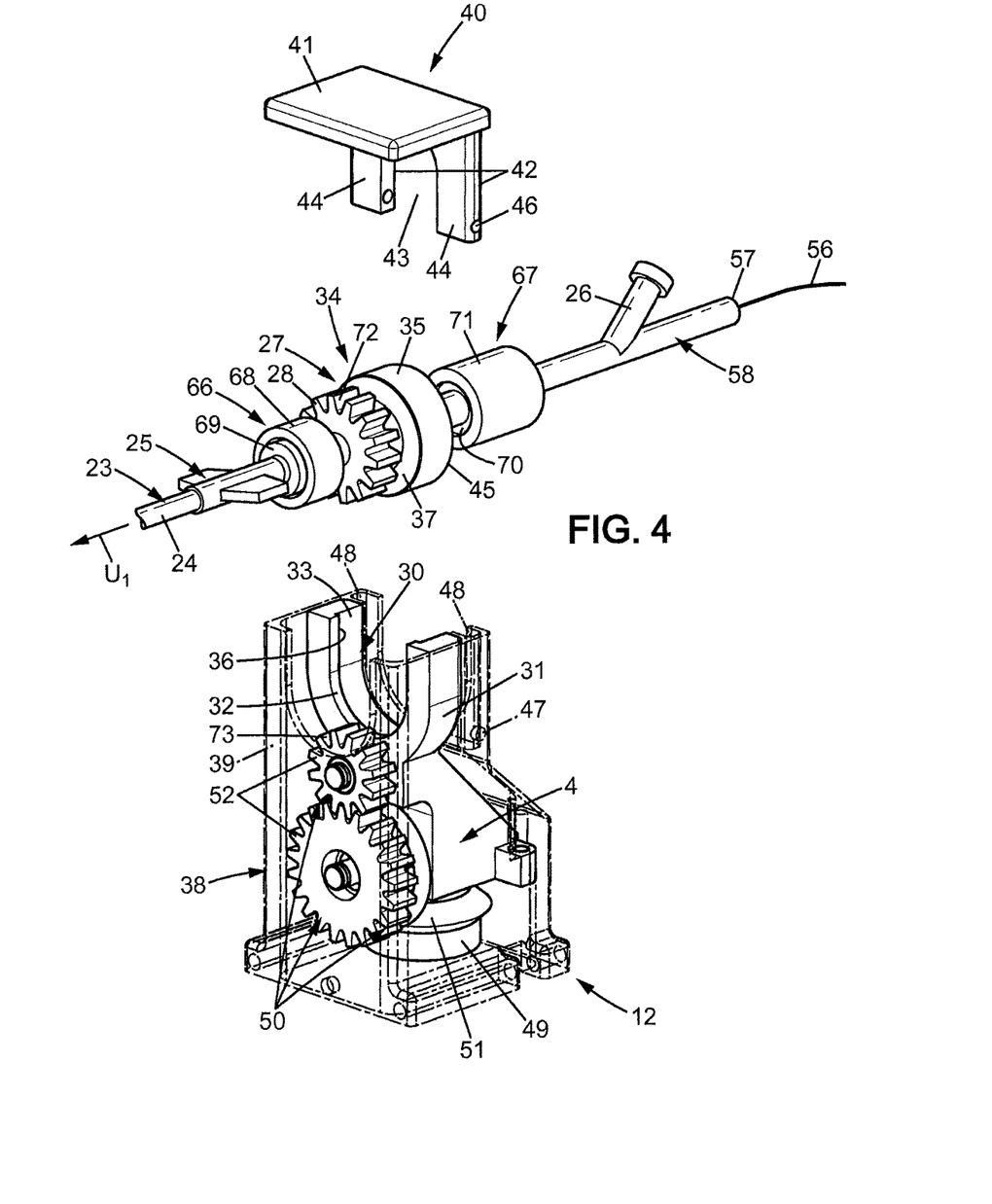
FIG. 4 is a partial perspective view of the drive module of FIG. 3 associated with a catheter.

The drive module 12 shall now be presented in more detail in relation with FIGS. 3 and 4.

The drive module 12 is fixed to the recipient 11 and is for example installed in the recipient 11 as shown.

The recipient 11 (FIG. 2) comprises a housing 59 comprising a bore 60 for axis motor passage. The drive module 12 is fixed to the recipient 11 above this bore 60. The drive module is for example fixed in a removable manner. A system of locking makes it possible to fix the drive module 12 to the recipient 11. A control lever 61 makes it possible to pass the locking system from the locked state wherein the drive module 12 is fixed to the recipient 11 to the unlocked state wherein the drive module 12 is able to be made rigidly connected to the recipient 11. Recourse is made for example to trigger guards 63 rigidly connected to the recipient 11 and receiving rods 64 of the drive module. The rods are movable relative to the casing 38 between an active position in which they extend in the trigger guard (locked configuration), and a free position in which they do not extend in the trigger guard (unlocked configuration).

An elastic element stresses the rods towards their active position.

The rods are rigidly connected to the levier 61, which can be actuated by a user in order to displace the rods towards the free position against the solicitation of the spring. The lever 61 has a grasping surface 65 for a main of a user.

The catheter 23 comprises on the one hand an elongate flexible body 24 and an end cap 25 rigidly connected to this elongate flexible body.

The end cap 25 is rigidly connected to a drive part 27 suited to cooperate with the drive module 12. For example, the drive part 27 comprises a gear 28 of axis U1 comprising a central hole in communication with the hollow inside of the catheter 23, and through which passes the guide 56. The gear 28 also comprises an external drive surface 72. The drive module 12 is suited for guiding the rotation of the catheter 23 around the axis U1 relative to it, while still fastening the catheter in translation with it according to this axis U1. To this effect, purely illustrative means shall be described hereinbelow.

Downstream of the drive part 27, a connector 58 rigidly connected to the latter can be provided. The connector 58, hollow, allows for the passage of the guide 56 through it and to the hole of the gear 28. It can comprise a bypass inlet 26 making it possible to place the inside of the catheter 23 in fluidic communication with an external circuit, for example for the injection of contrast fluid inside the body 24.

The guiding in rotation of the catheter 23 relative to the drive module 12 around the axis U1 can be provided by a bearing 30. The bearing 30 can comprise a calliper 31 that has a guiding surface 32 that is partially cylindrical in revolution, as well as a passage opening 33.

The bearing 30 can also comprise a continuous closed cylindrical ring 34. The ring 34 is part of the drive part 27. For example, the ring 34 is arranged downstream of the gear 28. The ring 34 is of axis U1 and comprises a central hole in communication with the hole of the gear 28. The ring 34 comprises an outer peripheral surface 35 cylindrical in revolution able to cooperate with the guiding surface 32 in order to guide in rotation the ring 34 with respect to the calliper 31 about the axis U1. The ring 34 is of a reduced diameter in such a way as to be able to pass through the passage opening 33.

The calliper 31 comprises a front abutment surface 36 forming a front abutment for the ring 34. In particular, the front abutment surface 36 is directed towards the rear and faces a front abutment surface 37 directed towards the front of the ring 34.

"Front" here refers to the direction U1 in the direction indicated by the arrow in FIG. 4, which corresponds to a forward movement inside the patient. "Rear" refers to a withdrawal movement from inside the patient.

The drive part 27 is rigidly connected to the catheter 23 by any suitable means. For example, it is connected to the cap 25 by a mechanical assembly 66, as shown in FIG. 4. The mechanical assembly 66 is hollow, comprising a hole in communication with the hole of the catheter and that of the gear 28. The mechanical assembly 66 comprises a first fastening portion 68, connected to the gear 28, and a second fastening portion 69, connected to the cap 25. The first fastening portion is upstream of the gear 28. Alternatively, the drive part 27 is of the same piece with the cap 25. The gear 28 is connected to the catheter 23.

The drive part 27 is connected to the connector 58 via any suitable means. For example, it is connected to the connector 58 by a mechanical assembly 67, as shown in FIG. 4. The mechanical assembly 67 is hollow, comprising a hole in communication with the hole of the connector 58 and that of the gear 28. The mechanical assembly 67 comprises a first fastening portion 70, connected to the gear 28, and a second fastening portion 71, connected to the connector 58. The first fastening portion 70 is downstream of the gear 28, and in particular downstream of the ring 34. Alternatively, the drive part 27 is of a single piece with the connector 58. Where applicable, the mechanical assembly 67 allows for the rotation of the drive part 27 relative to the connector 58 about the axis U1, while still maintaining the seal for the purposes of fluidic communication.

Where applicable, the two fastening portions of the drive part 27 are complementary with one another. That is to say that it is possible to assemble one of the fastening portions of the drive part 27 with the other of the fastening portions of another drive part 27. For example, the fastening portion 70 is identical to the fastening portion 69. For example, the fastening portion 68 is identical to the fastening portion 71. As such, starting from a standard catheter and connector, which can be assembled together via cooperation of the fastening portion 69 and of the fastening portion 71, the drive part 27 can be used as an added consumable medical device inserted between the catheter and the connector.

The drive module 12 also comprises a rear abutment system for the catheter 23, and a system for closing the passage opening 33. In the example shown, these two systems use a single and same part, but this embodiment is illustrative, and other means for implementing these two functions can be considered alternatively.

In the example shown, the drive module 12 comprises a casing 38 in two parts, a lower part 39, and an upper part 40 able to be made rigidly connected to one another by a system for closing. The lower part 39 comprises at least the calliper 31. In the open configuration, shown in FIG. 4, the catheter 23 connected to the ring 34 and to the gear 28 can be placed in position in the drive module 12 through the passage opening 33, or removed from this position. In closed configuration, or assembled, shown in FIG. 3 (without the catheter or the assembly 66), the lower 39 and upper 40 parts are assembled to one another in order to close the passage opening 34, and prohibit the catheter 23 from exiting the drive module. This closed configuration can therefore be used during the medical intervention. Where applicable, the system shown in FIG. 3, comprising the drive module 12 and the drive part 27 is carried out as a single-use consumable item that can be mounted/removed from the receptacle 3.

For example, the upper part 40 comprises a cover 41 from which extend two lateral arms 42 separated from one another by forming a slot 43 between them. In closed configuration, the drive part 27 rigidly connected to the catheter 23 extends into the slot 43. The arms 42 comprise a rear abutment surface 44 directed towards the front and forming an abutment surface for a rear abutment surface 45, directed towards the rear of the ring 34.

The closing system can include any suitable means. For example, a pin (not shown) is provided extending in the holes 46, 47 placed in correspondence with one another of the lower part 39 and of the upper part 40, respectively.

The lower part 39 can also comprise a system for guiding the cover 41 between the open and closed configurations. The guiding system can for example comprise two grooves 48 extending according to a direction transversal to the axis U1, for example according to the axis Z, and each cooperating with a respective arm 42.

The carter 38 also receives a drive system in rotation of the catheter 23, making it possible for a rotational command imparted remotely generates a rotation of the catheter around the axis U1.

In the purely illustrative example shown, the rotational command of the catheter 23 comes from a shaft 49 extending through the bore of passage 60 according to an axis different from the axis U1, for example a vertical axis. A transfer system 50 is provided that transfers the rotational movement of the shaft 49 to the gear 28. This transfer system can include a bevel gear 51 for transforming a rotational movement of axis Z to a rotational movement of axis parallel to the axis U1, and intermediate pinions 52 for transmitting rotational movements of axes parallel to the axis U1. The last intermediate pinion 52 of the kinematic chain comprises an outer drive surface 73 complementary with the drive surface 72 of the gear 28.

In the example shown, the guide 56 is introduced co-axially to the catheter 23 at the rear end of the latter, by the intermediary of the rear end 57 of the connector 58 rigidly connected to the latter.

The embodiment that has just been presented can operate as follows:

We begin with a method for installing the system.

A catheter 23 is provided with a cap 25. The drive part 27 is assembled to it (comprising the portion of fastening 68, the gear 28, the ring 34 and the portion for fastening 70). This assembly is carried out by assembling the fastening portion 68 to the fastening portion 69 connected to the cap 25. To the drive part 27 is assembled the connector 58. This assembly is carried out by assembling the fastening portion 70 to the fastening portion 71 connected to the connector 58. Where applicable, the catheter 23 is supplied as origin with the gear 28, the ring 34, even with the connector 58 incorporated.

AS the carter is in open configuration, the assembly formed by the catheter 23, the drive part 27 and the connector 58 is placed in the drive module 12, with the ring 34 in the calliper 31, and the gear 28 in cooperation with the transfer system 50. The catheter 23 is arranged in the receptacle 3, for example in the recipient 11, with a front end extending beyond the port 5. The catheter 23 is made integral in translation with the drive module 12 by placing the carter 38 in closed configuration. As such, by "integral", unless it is clearly not the case when reading the detailed description, reference is generally made to the fact that two parts are assembled to one another in such a way that a movement of one part according to any degree of freedom is transmitted to the other part. In this case, by exception, the catheter is connected to the drive module only in translation, namely the displacement of the catheter according to the axis U1 is linked to that of the drive module 12. However, these two parts are not integral in rotation around the axis U1.

The guide 56 is also installed and it is made to pass through the inside of the catheter 23 through an access opening 57 of the connector 58.

The robot 1, and the assembly formed of the catheter 23 and of the drive part 27, even of the connector 58, together, form what is called a robotic system in this text.

Once this guide and the catheter introduced inside the duct of the patient, there is an operating configuration, and one can proceed in the following way.

A displacement of the guide alone can be generated (translation and/or rotation) by means of the drive module 8.

In order to generate a displacement in rotation of the catheter alone around its longitudinal axis, the rotation of the shaft 49 is controlled by a dedicated motor carried under the receptacle, which generates the rotation of the gear 28 by the intermediary of the transfer system 50 and, consequently, the rotation of the catheter 23 connected to the gear 28.

In order to generate a displacement in translation of the catheter 23, the motor 54 causes the displacement (for example the rotation) of the receptacle 3 relative to the base 2. In order to generate a movement in the forward direction of the catheter 23 in the duct of the patient, the receptacle 3 is turned relative to the base 2 in the anticlockwise direction in FIG. 2. During this movement, the drive module 12 is displaced and the catheter 23, connected to the latter during this movement, is pushed towards the front. The deflector 17, which remains fixed as it belongs to the base 2, causes the catheter 23 to exit from the robot. The channel 6 guides the movement of the catheter outside of the robot in the direction of the patient. During this movement, either the guide is rigidly connected to the drive module 8, in which case the guide is also displaced in a forward movement. If it is desired to prevent this phenomenon, the translation control of the guide can be linked with the displacement control (rotation) of the receptacle 3 in order to generate an opposite movement of the guide relative to the receptacle 3. Alternatively, the guide is free of the drive module 8 during the displacement (of rotation) of the receptacle 3, in which case the drive module 8 slides on the guide without driving it during this displacement.

A displacement of the catheter 23 in the opposite direction is obtained by rotating the shaft 53 in the opposite direction.

Alternatively, the guide 56 could be introduced into the catheter 23 co-axially to the catheter 23 by an access opening arranged between the base 2 and the patient at the beginning of the intervention.

In case of an emergency, and regardless of the position of the catheter inside the patient, it is sufficient to place the cover 41 in open configuration in order to have access to the catheter 23 and remove it (with the drive part 27) from the robot 1.

As explained hereinabove, the drive part 27 could be rigidly connected to the catheter 23, and this component integrated (catheter+drive part) could be provided as a consumable item. Alternatively, the drive part 27 is maintained in the casing 38, and a catheter 23 is assembled therein for an intervention by the intermediary of the assembly 66. At the end of the intervention, the catheter 23 is disassembled from the drive part 27.

As such, according to the cases, the assembly comprising the assembly 66, the gear 28, the ring 34, the assembly 67 and the connector 58 can be carried out at a consumable component. Alternatively, each one of the parts, or of the subassemblies of several of these parts taken together, can be carried out as consumable items assembled in situ.

The invention therefore relates to an elongate flexible medical member comprising a flexible tube and a drive member rigidly connected to the flexible tube, and comprising a rotation drive portion that can be driven in rotation by a drive module in order to generate a rotation of the elongate flexible medical member about its longitudinal axis, and able to be connected in translation along the axis longitudinal to the drive module.

Where applicable, this drive member comprises a gear and a ring rigidly connected to the gear and able to guide the rotational movement by cooperation with a guiding calliper of the drive module.

According to an independent aspect, an invention could relate to an assembly comprising an elongate flexible medical member 23 comprising a flexible tube 24, with the assembly further comprising a drive part 27 connected to the flexible tube 24, and comprising a rotation drive portion 28 that can be driven in rotation by a drive module 12 in order to generate a rotation of the elongate flexible medical member 23 about its longitudinal axis U1, and able to be connected in translation along the axis longitudinal to the drive module 12.

According to a particular aspect, the drive part 27 comprises a gear 28 and a ring 34 rigidly connected to the gear 28 and susceptible to guide the rotational movement by cooperation with a guiding calliper 33 of the drive module 12.

According to a particular aspect, the assembly comprises an end cap 25 and/or a connector 58 rigidly connected to the drive part 27.

The invention claimed is:

1. A robotic catheterisation system, wherein the robotic catheterisation system comprises a catheter to be introduced inside a patient and a catheterisation robot,
    the catheter comprising a flexible tube and being connected to a rotation drive part, the rotation drive part comprising a gear connected to the flexible tube, having a hole and a first rotation drive surface, and a hollow connector connected to the drive part, downstream of the latter, and allowing for the passage of a guide through the connector and to the hole of the gear,
    with the catheterisation robot comprising:
        a fixed base,
        a receptacle mounted movable relative to the fixed base along at least one degree of freedom,
    the receptacle being suited to receive said catheter to be introduced inside a patient,
        a drive system suitable for driving the receptacle relative to the base along the degree of freedom,
    the receptacle further comprising a drive module, the drive module having a longitudinal axis for the passage of the catheter, with the drive module being connected to the catheter in translation along the longitudinal axis of passage in operational configuration of the robot, with the drive module comprising a rotation drive member comprising a pinion directly or indirectly motorised, and comprising a second rotation drive surface, the pinion meshing with the gear of the rotation drive part connected to the catheter, the drive module able to be actuated in order to generate a rotational movement of the catheter about the longitudinal axis of passage, the first and second rotation drive surfaces cooperating in order to transmit a rotational command from the rotation drive member to a rotational movement of the catheter about the longitudinal axis of passage.

2. The robotic system according to claim 1, wherein said rotation drive part comprises a first axial retention portion, and wherein the drive module comprises a second axial retention portion, with the first and second axial retention portions cooperating in order to axially retain the catheter relative to the drive module along the longitudinal axis of passage.

3. The robotic system according to claim 2, wherein the first axial retention portion of the rotation drive part comprises a first front abutment directed towards the front and a first rear abutment directed towards the rear,
    wherein the second axial retention portion of the drive module comprises a second front abutment, directed towards the rear, and a second rear abutment directed towards the front,
    wherein the first and second front abutments cooperate in order to prevent a displacement towards the front of the catheter relative to the drive module, and
    wherein the first and second rear abutments cooperate in order to prevent a displacement towards the rear of the catheter relative to the drive module.

4. The robotic system according to claim 1, wherein the drive part is carried out as a consumable part that can be assembled/disassembled from the drive module.

5. The robotic system according to claim 1, wherein the flexible tube is hollow.

6. The robotic system according to claim 1, wherein the drive part comprises an upstream mechanical assembly for assembly to the catheter, a gear, a ring, a downstream mechanical assembly for assembly to a connector for the introduction of the guide, and wherein the upstream mechanical assembly, the gear, the ring or the downstream mechanical assembly, or a component comprised of at least two of these elements is carried out as or is part of a consumable item that can be assembled/disassembled from the drive module.

7. The robotic system according to claim 1, wherein the drive module comprises a body and a cover mounted removably relative to the body, with the cover able to alternatively take, relative to the body, an assembled configuration wherein the drive module is rigidly connected to the catheter in translation along the longitudinal axis of passage, and an open configuration wherein the catheter can be assembled to or disassembled from the drive module.

8. The robotic system according to claim 1, wherein the base defines a channel comprising a guiding wall of the catheter, with the guiding wall cooperating with the catheter in order to guide a movement of translation of the catheter relative to the base during the movement of the receptacle relative to the base along the degree of freedom.

9. The robotic system according to claim 1, wherein the receptacle comprises a recipient suited to receive said catheter, the drive module being fixed to the recipient.

10. The robotic system according to claim 1, wherein the catheter is a first catheter, the drive module is a first drive module, with the robotic system further comprising a second elongate flexible member to be introduced inside the patient, with the receptacle being suited to receive said second elongate flexible member to be introduced inside a patient,
    the receptacle further comprising a second drive module, the second drive module able to be actuated in order to generate two separate movements of translation and of rotation of the second elongate flexible member relative to the receptacle.

11. The robotic system according to claim 10, wherein the first catheter comprises an access opening through which the second elongate flexible member extends.

12. The robotic system according to claim 10, wherein the receptacle comprises a recipient, wherein the second drive module is fixed to the recipient, and wherein the second drive module can be actuated in order to generate the movements of the second elongate flexible member relative to the recipient.

13. The robotic system according to claim 1, wherein the drive module is carried out as or being a part of a consumable item that can be assembled/disassembled from the recipient.

14. A catheterisation robot wherein the catheterisation robot comprises the features of the catheterisation robot of the robotic system such as defined of claim 1.

15. A rotation drive part wherein the rotation drive part comprises:
   a fastening portion suited for fastening the rotation drive part to a flexible tube of an upstream hollow catheter,
   a gear connected to the fastening portion, having a central hole intended to be in communication with the hollow inside of the flexible tube, and a first rotation drive surface,
   a secondary fastening portion suited for fastening the rotation drive part to a hollow connector downstream, and allowing for the passage of a guide wire through the connector to the hole of the gear,
   a robotic catheterisation system, wherein the robotic catheterisation system comprises the catheter to be introduced inside a patient and a catheterisation robot, the catheter comprising the flexible tube and being connected to the rotation drive part,
   the robotic catheterisation system further comprising:
      said catheter and the flexible tube and being connected to the rotation drive part, having a hole and the first rotation drive surface,
   the catheterisation robot further comprising
      a fixed base,
      a receptacle mounted movable relative to the fixed base along at least one degree of freedom, the receptacle being suited to receive said catheter to be introduced inside a patient,
      a drive system suitable for driving the receptacle relative to the base along the degree of freedom,
      the receptacle further comprising a drive module, the drive module having a longitudinal axis for the passage of the catheter, with the drive module being connected to the catheter in translation along the longitudinal axis of passage in operational configuration of the robot, with the drive module comprising a rotation drive member comprising a pinion directly or indirectly motorised, and comprising a second rotation drive surface, the pinion meshing with the gear of the rotation drive part connected to the catheter, the drive module able to be actuated in order to generate a rotational movement of the catheter about the longitudinal axis of passage, the first and second rotation drive surfaces cooperating in order to transmit a rotational command from the rotation drive member to a rotational movement of the catheter about the longitudinal axis of passage.

16. The rotation drive part according to claim 15, wherein the gear has an axis, the rotation drive part further comprising a continuous closed cylindrical ring comprising a central hole in communication with the hole of the gear, and suited for guiding the rotary drive part around said axis.

17. The rotation drive part according to claim 16, wherein the ring is downstream of the gear.

18. The rotation drive part according to claim 16, wherein the ring is upstream of the fastening portion.

19. The rotation drive part according to claim 16, wherein the ring comprises an outer peripheral surface cylindrical of revolution for guiding.

20. The rotation drive part according to claim 16, wherein the ring comprises a front abutment surface directed towards the front of the ring and a rear abutment surface, directed towards the rear of the ring.

21. The rotation drive part according to claim 15, wherein the fastening portion is suited for fastening the rotary drive part to the connector by allowing for the rotation of the drive part relative to the connector around a longitudinal axis, while still maintaining the seal for the purpose of fluidic communication.

22. The rotation drive part according to claim 15, wherein the fastening portions are complementary with one another.

23. A system, wherein the system comprises a rotation drive part according to claim 15 and a connector rigidly connected to the rotation drive part, allowing for the passage of a guide wire through the connector and to the hole of the gear,
   the connector comprising a fastening portion suited for cooperating with the fastening portion of the rotation drive part in order to rigidly connect the rotation drive part to the connector.

24. A system according to claim 23 wherein the connector comprises an inlet bypass making it possible to place the inside of the hollow catheter in fluidic communication with an external circuit for the injection of contrast fluid inside the flexible tube.

25. A system according to claim 23 with the system further comprising a hollow catheter provided with a flexible tube and with a fastening portion, suited for cooperating with the fastening portion of the rotation drive part in order to connect the rotation drive part to the flexible tube.

26. A system comprising a rotation drive part according to claim 15, with the system further comprising a hollow catheter provided with a flexible tube and with a fastening portion, suited for cooperating with the fastening portion of the rotation drive part in order to connect the rotation drive part to the flexible tube.

27. A robotic catheterisation system, wherein the robotic catheterisation system comprises a catheter to be introduced inside a patient and a catheterisation robot,
   the catheter comprising a flexible tube and being connected to a rotation drive part, the rotation drive part comprising a gear connected to the flexible tube, having a hole and a first rotation drive surface, and a hollow connector connected to the drive part, downstream of the latter, and allowing for the passage of a guide through the connector and to the hole of the gear, said gear comprising a central hole in communication with the hollow inside of the catheter,
   with the catheterisation robot comprising:
      a fixed base,
      a receptacle mounted movable relative to the fixed base along at least one degree of freedom,
   the receptacle being suited to receive said catheter to be introduced inside a patient,
      a drive system suitable for driving the receptacle relative to the base along the degree of freedom,
   the receptacle further comprising a drive module, the drive module having a longitudinal axis for the passage of the catheter, with the drive module being connected to the catheter in translation along the longitudinal axis of passage in operational configuration of the robot, with the drive module comprising a rotation drive member comprising a pinion directly or indirectly motorised, and comprising a second rotation drive surface, the pinion meshing with the gear of the rotation drive part connected to the catheter, the drive module able to be actuated in order to generate a rotational movement of the catheter about the longitudinal axis of passage, the first and second rotation drive surfaces cooperating in order to transmit a rotational command from the rotation drive member to a rotational movement of the catheter about the longitudinal axis of passage.

* * * * *

UNITED STATES PATENT AND TRADEMARK OFFICE
CERTIFICATE OF CORRECTION

PATENT NO. : 10,449,007 B2  
APPLICATION NO. : 15/322414  
DATED : October 22, 2019  
INVENTOR(S) : Sébastien Deboeuf et al.

Page 1 of 1

It is certified that error appears in the above-identified patent and that said Letters Patent is hereby corrected as shown below:

On the Title Page

Item (30) please add:  
--Foreign Application Priority Date: June 27, 2014 FR 14 56042--

Signed and Sealed this  
Thirty-first Day of December, 2019

Andrei Iancu  
*Director of the United States Patent and Trademark Office*